United States Patent [19]
Rutland

[11] Patent Number: 5,919,417
[45] Date of Patent: Jul. 6, 1999

[54] DUCT CLEANING METHOD

[76] Inventor: Earl E. Rutland, 1301 Lemmonwood Rd., Jacksonville, Fla. 32259

[21] Appl. No.: 08/892,753

[22] Filed: Jul. 15, 1997

[51] Int. Cl.$^6$ ...................................................... A61L 2/20
[52] U.S. Cl. .............................................................. 422/28
[58] Field of Search ................................ 422/186.07, 28

[56] References Cited

U.S. PATENT DOCUMENTS

| | | | |
|---|---|---|---|
| 5,160,481 | 11/1992 | Weaver | 422/186.07 |
| 5,173,268 | 12/1992 | Weaver | 422/186.15 |
| 5,525,310 | 6/1996 | Decker | 422/189.07 |
| 5,573,730 | 11/1996 | Gillum | 422/123 |
| 5,667,563 | 9/1997 | Silva, Jr. | 96/50 |
| 5,681,533 | 10/1997 | Hiromi | 422/121 |
| 5,759,487 | 6/1998 | Jung | 422/22 |

*Primary Examiner*—Daniel J. Jenkins
*Attorney, Agent, or Firm*—Ronald E. Smith

[57] ABSTRACT

An ozone generator is formed by extending an elongate coil spring through an elongate cylindrical tube. Several return bends are formed in the coil spring to provide several continuous straight sections that extend the length of the tube. A conductive foil overlies the tube so that electrical discharges are created between radially outermost parts of the coil spring and an inner surface of the tube when a potential difference is established between the spring and foil. The tube is made of a dielectric material to prevent direct arcing between the spring parts and the foil. The device operates from household current and produces ozonated air when air is blown through the tube. In one application, a closed circuit is established that includes air conditioning ducts in series with the ozone generator and a blower so that dwelling occupants are protected from ozone inhalation as the ozone destroys respiratory problem-causing organisms living in the ducts.

1 Claim, 4 Drawing Sheets

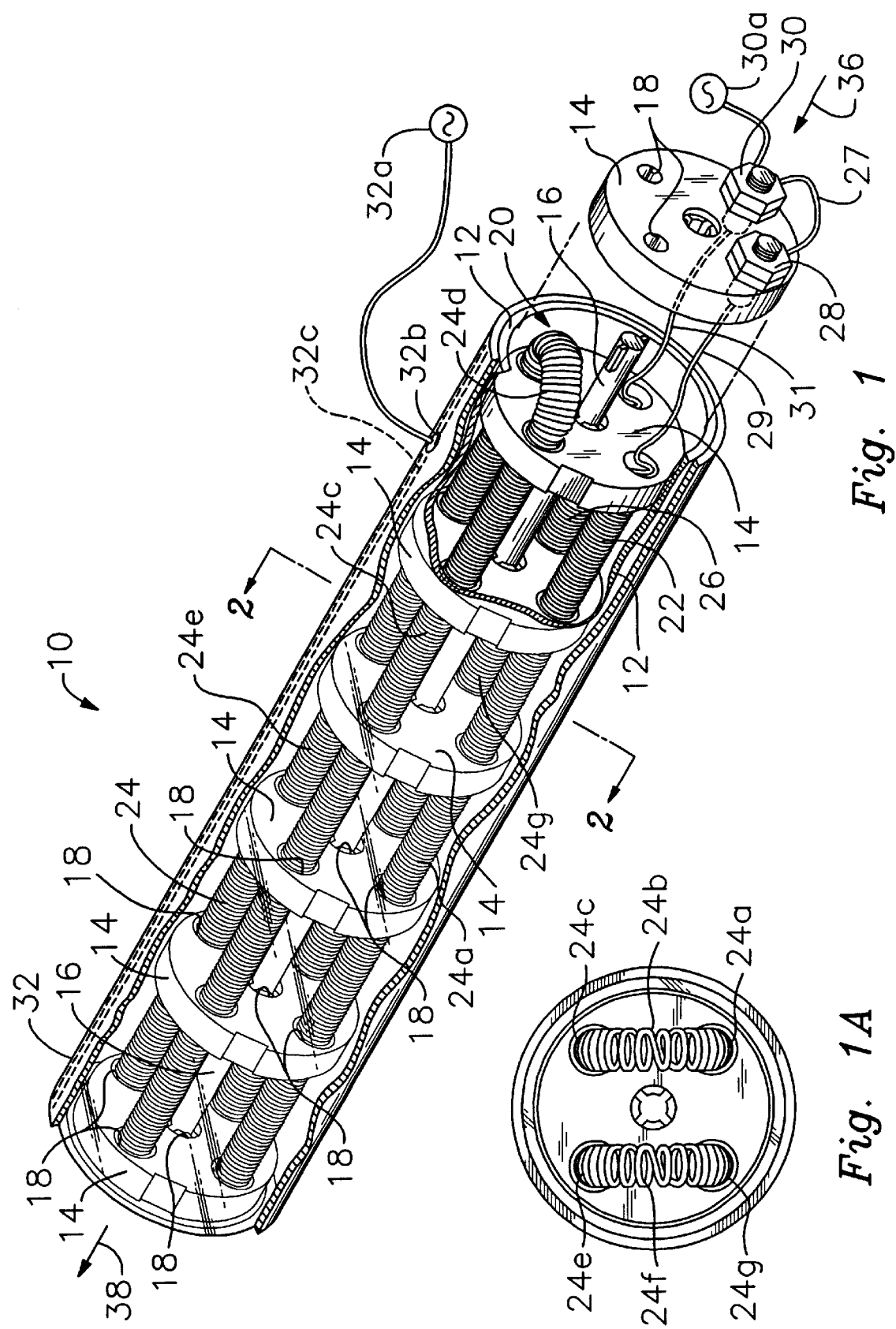

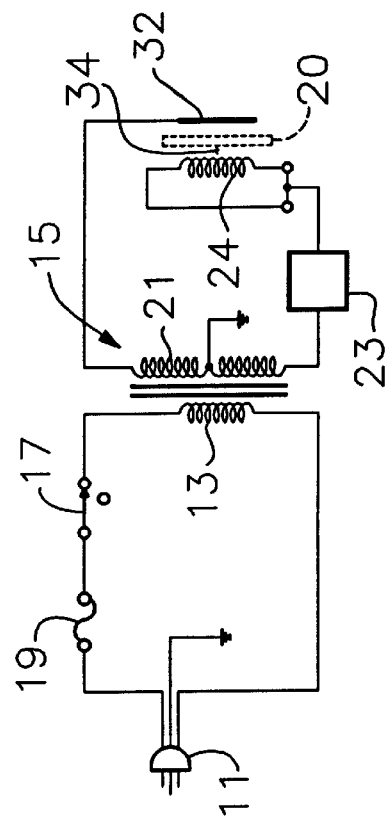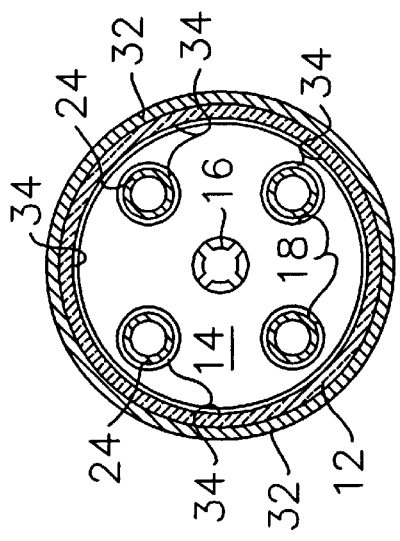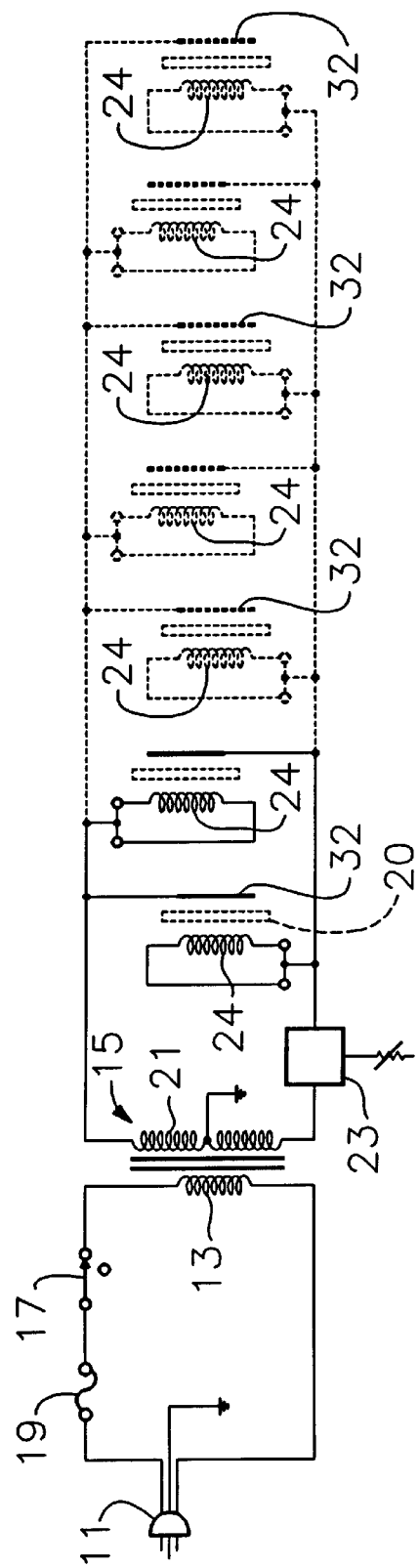

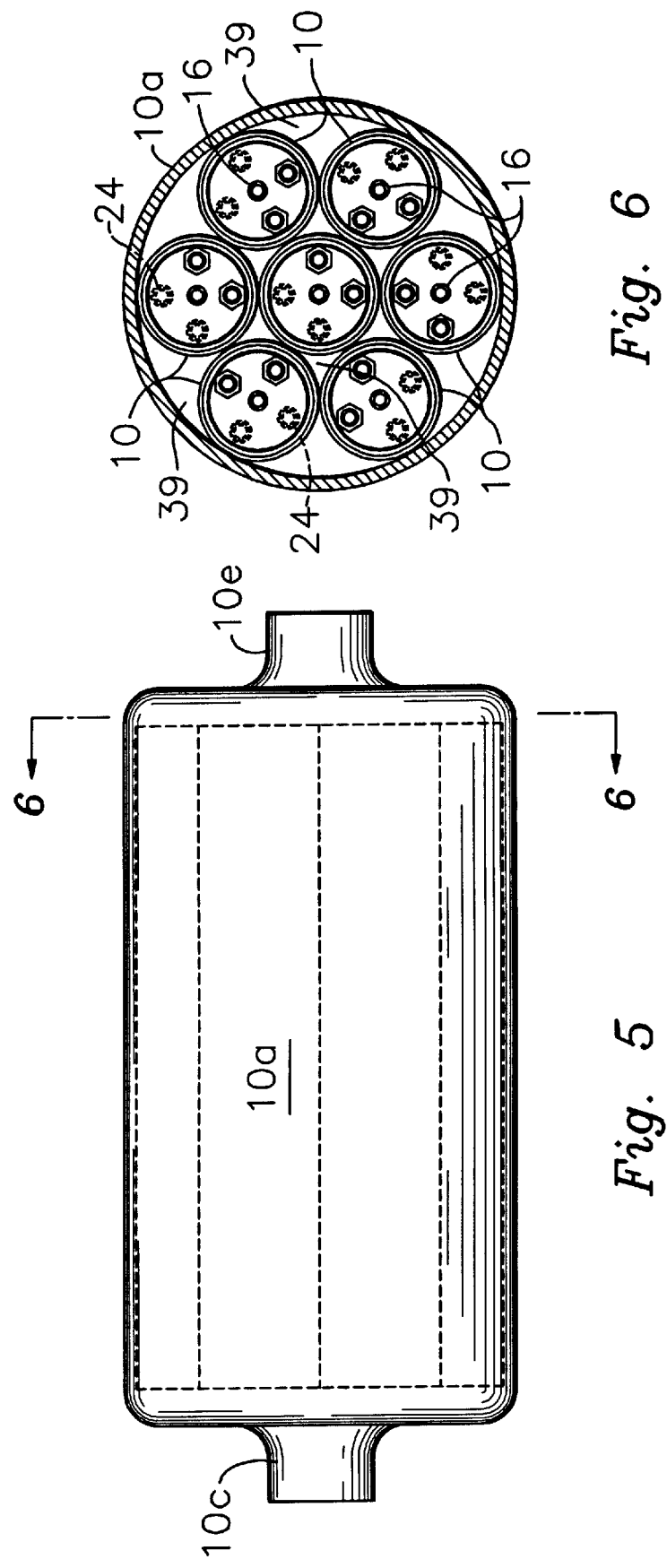

DUCT CLEANING METHOD

BACKGROUND OF THE INVENTION

1. Field of the Invention

This invention relates, generally, to ozone generators. More particularly, it relates to a household current-driven ozone generator including a coil spring and a method for cleaning air conditioning ducts with ozonated air.

2. Description of the Prior Art

Ozone may be generated by placing a sufficient potential difference between two spaced apart electrodes to cause a discharge between them, positioning an insulator between the electrodes to prevent direct arcing between them, and passing oxygen or a gaseous mixture containing oxygen between the two electrodes when discharges are occuring. The discharge converts $O_2$ (a molecule of oxygen) to $O_3$ (a molecule of ozone).

Ozone may be used in numerous applications, all relating to its ability to destroy bacteria and to deactivate viruses. Thus, it can be used to purify water, destroy odors, and the like.

Since ozone generators consume electrical power, the primary developments over the years have related to methods for increasing the efficiency of the devices, i.e., for increasing the quantity of ozone created per unit of power consumption.

The conventional wisdom, reflected in Japanese patent No. 59-111902 (1984), is that the best way to increase efficiency is to operate the devices at high frequencies. For example, that patent discloses a device that operates at a pulse width of 1000 nanoseconds or less. A power source capable of producing a high voltage of such short pulse width is expensive.

What is needed, then, is an ozone generator that produces ozone in ample quantities but which operates at sixty cycles per second, i.e., at household current frequency. Such a device would be affordable because it would not require a special power supply. If it could be provided in portable form, it could be put to numerous consumer applications.

There is a need as well for an ozone generator that is made of low cost, commercially available parts.

However, in view of the prior art considered as a whole at the time the present invention was made, it was not obvious to those of ordinary skill in this art how such a device could be provided.

SUMMARY OF THE INVENTION

The longstanding but heretofore unfulfilled need for an apparatus that overcomes the limitations of the prior art is now met by a new, useful, and nonobvious invention. The novel ozone generator includes an elongate tube made of a dielectric material such as glass; the tube has a cylindrical inner surface, a first end, and a second end. A thin foil of a preselected conductive material such as aluminum, brass, copper, and the like is wrapped around a cylindrical outer surface of the tube in overlying relation thereto, and an elongate coil spring is disposed within the tube, in parallel relation to a longitudinal axis of symmetry of the tube and in predetermined spaced relation to the elongate tube and the thin foil of conductive material. The foil is easily attached to the tube if it is provided with an adhesive backing.

The elongate coil spring is formed of a plurality of integrally formed helical parts of equal diameter and equal helical extent. A plurality of spacers are provided for holding the elongate coil spring in said parallel relation; the spacers are disc-shaped and are formed of a dielectric material. The spacers are positioned within the tube, and each spacer has an outer diameter substantially equal to an inner diameter of the tube so that each spacer fits snugly within the tube and so that each spacer can be selectively repositioned within the tube along the longitudinal extent thereof.

Each spacer has one or more apertures formed therein to receive the coil spring therethrough.

The device further includes means for applying a potential difference across the thin foil of conductive material and the elongate coil spring. The potential difference is of sufficient value to cause an electrical discharge between a radially outermost point on each of the helical parts of the coil spring and the cylindrical inner surface of the tube; the discharge cannot reach the thin foil of conductive material due to the presence of the tube.

The means for applying the potential difference includes a source of alternating current and a transformer having a primary winding in electrical communication with said source. The transformer has a center-tapped secondary winding; a first end of the secondary winding is in electrical communication with the thin foil of conductive material, and a second end of the secondary winding is in electrical communication with the elongate coil spring. Accordingly, alternating current applied to the thin film of conductive material is out of phase with alternating current applied to the elongate coil spring. This causes arcing across the space between the radially outermost point of each helical turn of the spring and the inner cylindrical surface of the tube. A linear conductor extends the length of the tube, in underlying relation to the conductive foil so that the voltage applied to a first end of the conductive foil is substantially the same along its entire extent.

A suitable means for blowing a gaseous fluid including oxygen or air containing oxygen into the first end of the tube is also provided, together with means for collecting a gaseous fluid including ozone from the second end of the tube.

Significantly, when a gaseous fluid such as oxygen or air containing oxygen is blown through the tube, the gaseous fluid is constrained to flow through the apertures formed in the spacers for receiving the coil spring. This causes turbulence in the gaseous fluid as it flows through the apertures, thereby mixing the gaseous fluid thoroughly and thereby enhancing the efficiency of the novel device. In this way, the number of spacers in the device determines the number of stages in the device, with the gaseous fluid being increasingly mixed as it proceeds from each stage of the device to the next.

The invention also includes an ozone generator made up of a plurality of the novel generators; said generators are collectively positioned in a housing with heat insulating means between them. The housing includes an input and an output so that it may be used in the same way as the single tube ozone generator of this invention. Its utility lies in those applications requiring high volume flows of ozone.

One unique application for harnessing the ozone generated by the novel generator is a method of cleaning air conditioning ducts. The novel method includes the steps of positioning a first fitting on a return air register, extending a conduit from the first fitting to an output of an ozone generator, positioning a second fitting on a supply air register, extending a conduit from the second fitting to an input of the ozone generator, and providing circulating means for circulating air from the output of the ozone generator, through an air conditioning duct, and to the input of the ozone generator so that air circulating through the air conditioning duct is ozonated when the ozone generator is operating.

It is a primary object of this invention to provide a high efficiency ozone generator made from readily available parts so that expensive power supplies and the like are not required.

Another object is to provide a high efficiency ozone generator that is powered by ordinary household current.

Another object is to provide a method whereby ozone could be safely employed in various consumer applications such as cleaning residential or industrial air conditioning ducts.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a perspective view of the novel ozone generator of this invention;

FIG. 1A is an end view thereof;

FIG. 2 is a sectional view taken along line 2—2 in FIG. 1;

FIG. 3 is an electrical schematic of the device of FIG. 1;

FIG. 4 is an electrical schematic of a device that incorporates multiple ozone generators of the type depicted in FIG. 1;

FIG. 5 is a side elevational view of a device that incorporates multiple ozone generators of the FIG. 1 type;

FIG. 6 is an end view of the device depicted in Fig. 5; and

DETAILED DESCRIPTION OF THE PREFERRED EMBODIMENT

Figure 7:
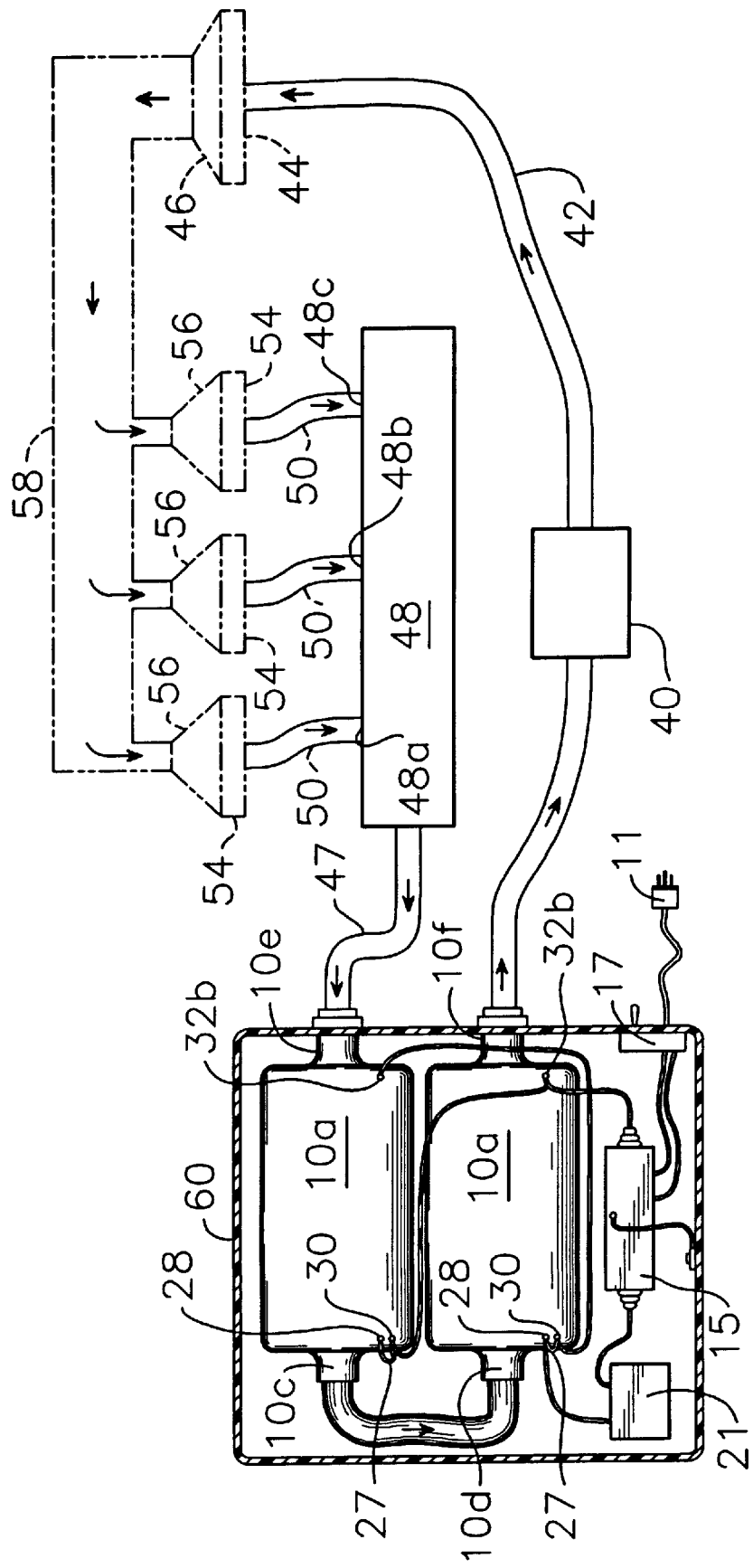
FIG. 7 is a diagrammatic view of an air conditioning duct cleaning system that incorporates two of the devices depicted in FIG. 5.

Referring now to FIG. 1, it will there be seen that an exemplary embodiment of the invention is denoted as a whole by the reference numeral 10.

Ozone generator 10 includes an elongate tube 12 having a plurality of disc-shaped spacers, collectively denoted 14, disposed at predetermined intervals along its length. Spacers 14 are formed of a dielectric material. Elongate rigid rod 16 is positioned coincident with the longitudinal axis of symmetry of elongate tube 12 and serves as a mounting means for spacers 14, i.e., each spacer 14 is centrally apertured to accommodate said rod 16. Each spacer may be positioned along the length of rod 16, so a designer for a particular application may select the number of spacers and the spacing between them. The outer diameter of each spacer 14 is substantially the same as the inner diameter of elongate tube 12 so that said spacers fit snugly therein. Significantly, gaseous fluid flowing through the novel device cannot flow around the outer perimeter of the spacers due to said snug fit.

In the illustrated embodiment, four additional apertures, collectively denoted 18, are formed in each spacer 14 in equidistantly spaced relation to one another and in circumferentially spaced relation to said longitudinal axis of symmetry. However, the number of apertures 18 may differ.

In a preferred embodiment, an elongate coil spring 20 has a first end 22, a main body 24, and a second end 26 disposed in transverse relation to said first end. First end 22 is conductively secured to first electrical terminal 28 by conductor 29 and second end 26 is conductively secured to second electrical terminal 30 by conductor 31. Conductor 27 interconnects terminals 28 and 30 to one another; note that alternating current having a first phase as at 30a is applied to terminals 28 and 30.

Main body 24 of coil spring 20 extends sequentially through all of the apertures 18 formed in all of the spacers 14. More particularly, a first straight section 24a of said elongate coil spring extends through a first set of longitudinally aligned apertures, and makes a first return bend 24b (FIG. 1A) at the end of the elongate tube remote from first and second terminals 28, 30. A second straight section 24c extends through a second set of longitudinally aligned apertures and makes a second return bend 24d (FIG. 1) at the end of the elongate tube proximal to said first and second electrodes. A third straight section 24e extends through a third set of longitudinally aligned apertures and makes a third return bend 24f (FIG. 1A) adjacent said first return bend 24b. A fourth straight section 24g extends through a fourth set of longitudinally aligned apertures and terminates at said second terminal 30. The number of straight sections and return bends will differ when a different number of apertures 18 are formed in spacers 14. Moreover, it should be appreciated that the novel device will also operate with no return bends at all, i.e., a single straight section of coil spring 20 may be provided, with only one aperture 18 being formed in spacers 14 to accommodate such single straight section. Such a simplified embodiment would produce a lower quantity of ozone than an embodiment having at least one return bend and hence at least two straight sections, but a low production of ozone may be desireable in some applications.

In all embodiments, coil spring 20 is continuous from first terminal 28 to second terminal 30; in a single straight section embodiment, second terminal 30 would be positioned at an end of tube 12 opposite to first terminal 28.

In the embodiment of FIG. 1, each of the four straight sections of coil spring 20 are parallel to one another and to rod 16. Each straight section is also disposed in closely spaced relation to the inner cylindrical side wall of elongate tube 12.

A thin foil 32 of electrically conductive material, such as aluminum, brass, copper, and the like, overlies the outer cylindrical surface of elongate tube 12. Such foil may be advantageously attached to said tube if said foil is provided with an adhesive backing.

An alternating current as at 32a is applied to foil 32 as at 32b; note that it is out of phase with the alternating current 30a applied to elongate coil 20.

Note that terminal 32b is positioned near a first end of tube 12; accordingly, the resistance of foil 32 could result in a lower voltage being applied to said foil at a remote end thereof. Accordingly, a linear conductor in electrical communication with terminal 32b extends along the length of tube 12, in underlying relation to foil 32; said linear conductor is denoted 32c in FIG. 1. It ensures that the voltage applied to foil 32 is substantially the same along its longitudinal extent.

Elongate coil spring 20 is of continuous structure, but may be thought of as being collectively formed of a plurality of truncate sections, each truncate section being defined by a 360° helical turn. All of said helical turns have a common longitudinal extent and diameter and are hereinafter referred to as helical parts.

As best understood in connection with FIG. 2, each discharge 34 extends from the radially outermost point of each helical part to the cylindrical inner side wall of elongate tube 12, i.e., each discharge extends radially outwardly from a point on each helical part that is closest to said cylindrical inner side wall. Thus, each discharge occurs along the shortest path between said cylindrical inner side wall and the outermost point of each helical part.

The high efficiency of this invention is achieved in large part due to the large numbers of helical parts that are provided by elongate coil 20. Moreover, the low cost of this invention is a function of the very low cost of elongate tube 12, spacers 14, and coil spring 20.

When air containing oxygen is introduced into elongate tube 12 at an inlet thereof, as indicated by directional arrow 36 at the right end of FIG. 1, air and ozone are recovered at an outlet thereof as indicated by directional arrow 38 at the left end of FIG. 1, when the novel device is in operation, i.e., when out-of-phase high voltage is applied to elongate coil 20 and said foil 32 as aforesaid. If the air and ozone mixture is recycled, i.e., fed back to the inlet of the novel device, the concentration of ozone and hence the efficacy of the device increases with the passage of time.

Significantly, the gaseous fluid flowing through tube 12 is turbulated because it is constrained to flow through apertures 18 formed in spacers 14 in order to flow from a first end of the device to a second end thereof. In this way, the amount of mixture of the gaseous fluid is increased as it flows from stage to stage of the device; this increases the efficiency of the device.

As indicated in FIG. 3, a one stage ozone generator 10, such as depicted in FIG. 1, is plugged into a grounded source of alternating current as at 11. Current flows through the primary winding 13 of a step-up transformer 15 when on-off switch 17 is closed; fuse 19 protects primary winding 13 from excess current flow. Secondary winding 21 of the transformer is center tapped as depicted; thus, out-of-phase high voltage is applied to elongate coil 20 and foil 32 as depicted. Preferably, the voltage is about 7,000 volts. A discharge occurs when coil spring 20 is negative and foil 32 is positive, and vice versa, i.e., there are sixty discharges per second at each helical part.

Box 23 represents a conventional current limiter that prevents excessive heat build-up in the circuit.

FIG. 4 is an electrical schematic depicting an ozone generator having multiple stages. All of the parts thereof are the same as in FIG. 3, there simply being more of the same. In this particular illustration, there are seven stages of ozone generators 10, connected in parallel to one another so that the potential difference across elongate coil 20 and foil 32 is the same for each stage.

An illustrative arrangement of seven stages of ozone generators that are grouped to collectively provide a high-output ozone source is depicted in FIGS. 5 and 6. It should be apparent that differing numbers of generators 10 could be grouped together as well. Housing 10a may be formed of polyvinylchloride or any other suitable material. An insulating material 39, such as an expanded foam or the like, fills the spaces between the generators 10 and inhibits heat transfer between them.

Alternatively, a heat-dissipating medium such as water or other suitable liquid mixture may be pumped through such spaces to cool the individual generators.

An illustrative assembly of parts that facilitates carrying out the steps of the novel method is depicted in FIG. 7. There it will be seen that two ozone generators 10a and 10b are connected in series to one another so that the output 10c of generator 10a is fed into the input 10d of generator 10b. Blower 40 is connected downstream of the output 10f of generator 10b; its compression side is in fluid communication via conduit means 42 with a fitting 44 adapted to sealingly engage return air register 46 and its suction side is in fluid communication with output 10f of generator 10b as depicted.

Input 10e of generator 10a is in fluid communication via conduit 47 with a manifold 48 having a plurality of inlets 48a, 48b, and 48c. Each manifold inlet is in fluid communication with a proximal end of a flexible conduit means 50. A fitting 54 is provided at the remote end of each conduit means 50; each fitting is adapted to sealingly engage a supply register 56.

To treat the air conditioning ducts 58 of a building, the novel steps include positioning a first fitting 44 in sealing relation to a return air register 46, connecting a first conduit 42 in fluid communication with said first fitting 44 to the compression side of a blower 40, connecting the suction side of the blower to the output 10f of an ozone generator, and connecting the input 10e of the ozone generator to a supply air register 56 by means of a second conduit 50 and a second fitting 54, In this way, no ozone is introduced into the living space of the air-conditioned structure because the first and second fittings 44 and 54, respectively, are sealingly engaged to the return air and supply air registers 46 and 56, respectively. As the closed circuit system operates, the ozone concentration increases because the output 10f of the generator is connected to the input 10e thereof. Thus, all living organisms such as bacteria, mold spores, fungi, viruses, and the like which might be living in the air conditioning ducts and which might be causing respiratory problems for the structure's occupants, are effectively destroyed. The closed circuit system prevents respiration of ozone by the occupants of the structure.

Housing 60 may be employed to house generators 10a and 10b and transformer 15 as well.

The novel ozone generator of this invention produces ozone in high quantitites at low power consumption. It is made of inexpensive parts, runs off household current, and can be easily repaired and maintained as needed.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of cleaning air conditioning ducts, comprising the steps of:

positioning a first fitting on a return air register;

extending a conduit from said first fitting to an output of an ozone generator;

positioning a second fitting on a supply air register;

extending a conduit from said second fitting to an input of said ozone generator; and providing circulating means for circulating air from said output of said ozone generator, through an air conditioning duct, and to said input of said ozone generator so that air circulating through said air conditioning duct is ozonated when said ozone generator is operating and so that ozone generated by said ozone generator circulates in a closed circuit defined by said ozone generator, said return air register, said air conditioning duct, and said supply air register;

whereby ozone is not discharged into air breathed by occupants of a structure within which said air conditioning ducts are mounted.

* * * * *